(12) United States Patent
Escano et al.

(10) Patent No.: US 6,279,368 B1
(45) Date of Patent: Aug. 28, 2001

(54) NITINOL FRAME HEATING AND SETTING MANDREL

(75) Inventors: Arnold M. Escano, Santa Clara; David T. Pollock, Redwood City, both of CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/589,670

(22) Filed: Jun. 7, 2000

(51) Int. Cl.⁷ .................................................. B21D 37/16
(52) U.S. Cl. .................. 72/342.1; 72/342.94; 72/370.08; 72/466.2
(58) Field of Search .................................. 623/1.15, 1.22, 623/11, 12, 1.17, 1.18, 1.19; 606/194, 195; 72/342.1, 342.94, 370.01, 370.06, 370.07, 370.08, 379.2, 466.2, 466.8

(56) References Cited

U.S. PATENT DOCUMENTS

| | | | |
|---|---|---|---|
| 5,707,388 | * | 1/1998 | Lauterjung .............................. 606/198 |
| 5,718,724 | * | 2/1998 | Goicoechea et al. ................ 623/1.15 |
| 5,746,765 | | 5/1998 | Kleshinski et al. . |
| 5,800,519 | * | 9/1998 | Sandock ..................................... 623/1 |
| 6,071,308 | * | 6/2000 | Ballou et al. ........................ 623/1.15 |

* cited by examiner

Primary Examiner—Ed Tolan
(74) Attorney, Agent, or Firm—Fulwider Patton Lee & Utecht, LLP (57) ABSTRACT

An apparatus for heating and setting a stent having curved limb elements. The apparatus is a mandrel having a restraining mechanism such as pins placed on the outer surface of the mandrel or shallow grooves machined in the outer surface of the mandrel to hold and mold the stent. The mandrel helps alleviate stresses induced upon stent elements during the heating and setting process and produces a more exact stent according to the desired stent design.

8 Claims, 8 Drawing Sheets

NITINOL FRAME HEATING AND SETTING MANDREL

BACKGROUND OF THE INVENTION

This application relates to heating and setting mandrels for use in manufacturing and more particularly, a mandrel for heating and setting a stent having limb members which provide for improved expansion characteristics.

The term stent generally refers to a prosthesis, which can be introduced into a corporeal lumen and expanded to support that lumen or attach a conduit to the inner surface of that lumen. Self-expanding stents are generally known in the art. During use, the self-expanding stent is compressed into a reduced size having an outer diameter substantially smaller than the stent in its expanded shape. The stent is held in its compressed state during its passage through the patient's vascular system until reaching the target treatment site, whereupon the compressed self-expanding stent may be deployed. While in its compressed state, stress is stored in the bends of the stent limbs. During deployment, the stresses in the stent limbs cause the stent to expand radially from its initially compressed state. Once in place, the radial extremities of the stent bear against the inside walls of the passageway, thereby allowing normal blood flow.

The processes of manufacturing self-expanding stents are also known in the art insofar as heating or annealing a stent upon a mandrel for purposes of setting a particular stent shape. Additionally, shape memorization processes utilizing mandrels are stent specific as each stent-type embody different design requirements. Previous attempts at heating or annealing simply involve mounting a stent upon a mandrel and exposing it to heat with little attention being paid to the shape that is set during the heating process. Because these previous attempts fail to control the shape created during the heating process, a less effective final stent is produced.

Most stents known in the art change diameter through the deformation of a small percentage of a length of the limbs defining the stent. Usually, this deformation occurs only at, or near, curved apices formed in stent limbs. The length of the limb that deforms and the magnitude of the deformation has a bearing on three important and interrelated characteristics of the stent: 1) the minimum diameter to which the stent can be compressed; 2) the radial stiffness or energy required to compress the stent; and 3) the maximum value of stress/strain experienced by the stent. Many other factors are also determinative of these characteristics including stent material, resting diameter, stent length, etc.; however, these other factors are assumed to be generally constant for a given stent design.

A stent having curved limb members can improve the above mentioned characteristics of the stent by spreading the deformation energy over a majority of the length of the stent limbs. This is in contrast to other stent designs that concentrate the deformation at or near the apices in the stent limb.

For example, to maximize radial stiffness and minimize a compressed diameter of a stent, limb elements defining the stent each can embody two curves of constant radius and opposite direction which meet at an inflection point. When such a stent is compressed, the two curved sections assume a nearly straight profile, the advantage of which is that the entire length of the curved portions store deformation energy and function to urge the stent radially outward.

In the event a stent having curved limb members is to be manufactured, in order to set a desired expanded configuration the stent is expanded over a cylindrical mandrel and heated. However, merely expanding the stent over a mandrel without additional controls or constraints, rarely results in limb elements having the desired profile. To wit, the end of the limbs may be provided with a smaller than desired radius of curvature whereas the portion of the limbs near an inflection point may have a much larger than desired radius of curvature. This results in producing a stent that embodies limbs which do not store stress in an optimal manner.

Therefore, what is needed and heretofore unavailable in the art is a mandrel for heating and setting a stent which facilitates the production of a desired stent profile as well as aids in evenly dispersing stresses along limb elements defining the stent during manufacturing. The present invention satisfies these and other needs.

SUMMARY OF THE INVENTION

Briefly, and in general terms, the present invention provides an improved heating/setting mandrel which substantially reduces the amount of stress inflicted upon the stent during the stent manufacturing process by having restraint mechanisms which properly shape the stent and effectively alleviate unwanted stresses imposed upon the stent limbs during the heating portion of the manufacturing process. Moreover, the mandrel construction of the present invention is relatively inexpensive to manufacture, is trouble-free and reliable in use, and attains improved and constant results in the manufacture of the an improved stent having curved limb elements.

Furthermore, the present invention provides increased radius of curvature values for the curved limb elements at or near the areas of a stent cell where limbs meet and decreased radius of curvature values near an inflection point of the stent limb. Therefore, the benefits of having stent limbs with one radius of curvature value along a first curve and the same but opposite radius of curvature value in a second curve is achieved.

In one aspect, the invention comprises a hollow cylinder made from a heat conducting material having restraint mechanisms to shape and hold in place a stent having curved limb elements. In this configuration, restraint mechanisms are strategically placed on the outer surface of the mandrel. These restraint mechanisms serve to force the stent into the desired shape and hold the stent limbs in place during the heating process.

In a preferred embodiment, the mandrel of the present invention embodies a hollow cylinder with a pattern of radially drilled holes on the outer surface of the mandrel that accepts a plurality of pins which constrain stent limbs in a desired configuration during the heating process. In another embodiment of the invention, the plurality of pins may be individually placed or made part of a mechanism that allows them to protrude and retract from the outer surface of the mandrel. In yet another embodiment, the mandrel of the present invention embodies a hollow cylinder with shallow grooves representative of a desired stent design pattern, the same being machined into the outer surface of the mandrel.

Other features and advantages of the present invention will become apparent from the following detailed description, taken in conjunction with the accompanying drawings, which illustrate, by way of example, the principles of the invention.

DETAILED DESCRIPTION OF THE INVENTION

The present invention is directed to an improved mandrel for use in heating and setting a stent having curved limb elements which alleviates the stresses inflicted upon the limbs of the stent during the manufacturing. The mandrel provides compressive restraints upon the limbs of the stent during the heating process by employing the use of constraint mechanisms which hold in place the limb portions of the stent to thereby produce a stent with limb portions having constant radius of curvatures.

Figure 1:
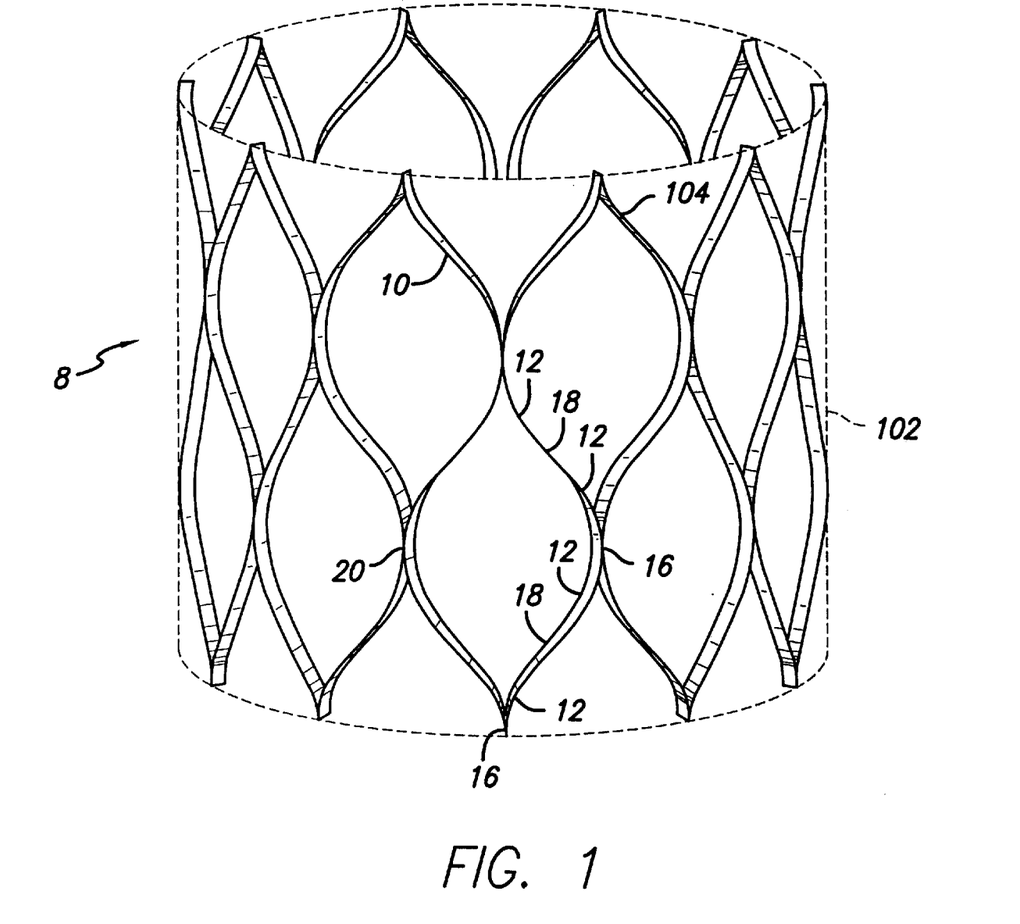
FIG. 1 is a perspective view with some elements in the background not shown for clarity, depicting a stent having curved limb elements to be manufactured with the present invention.
Figure 2:
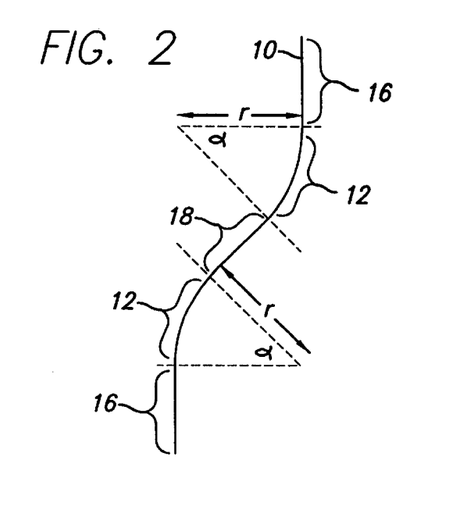
FIG. 2 is a side view, depicting a single curved limb element of the stent of FIG. 1.

Referring now to the drawings, in FIG. 1, there is shown an example of a stent 8 having curved limb elements to be manufactured with the present mandrel invention. Such a stent 8 may be cut from a tube or assembled from separate elements. FIG. 2 depicts a repeating element of each limb 10 of a stent cell, having two curved elements 12 of equal radius, equal length and opposite direction. The short straight segment element 16 at the ends of each limb 10 are parallel to one another. The mid-portion or the inflection point 18 lies between the two curved segment elements 12 of each stent limb 10.

Figure 3:
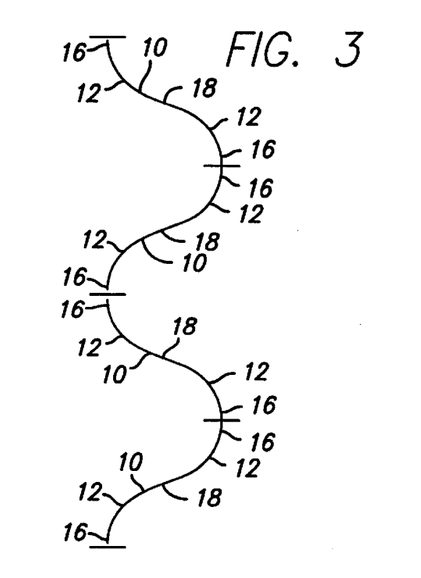
FIG. 3 is a side view, depicting a curved limb element of a stent to be used in the present invention.
Figure 4:
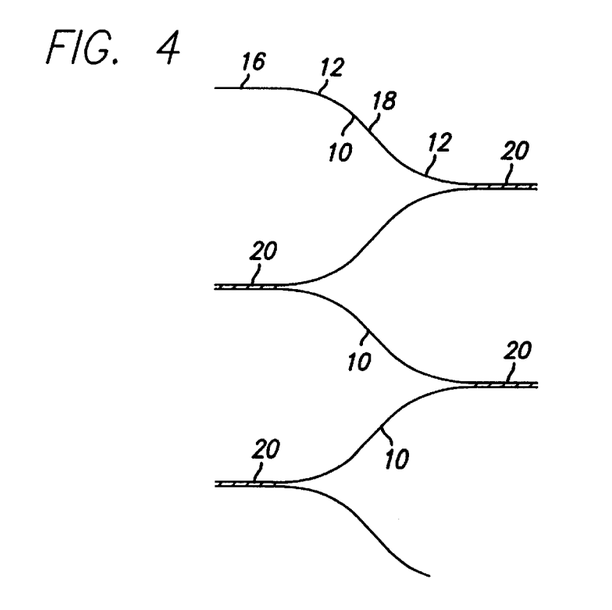
FIG. 4 is a side view, depicting typical joints between adjacent curved limb elements in a stent which is comprised of a multiplicity of such curved limb elements.

Referring to FIG. 3, depending on the overall length of the stent, the limb element 10 may bend back and forth in a sinusoid wave pattern down the length of the stent 8. Additionally, referring to FIG. 4, in the event the stent 8 is made from separate elements, the short straight segment elements 16 of adjacent limbs maybe joined, either by welding, soldering, riveting, or gluing to form joint 20. A multiplicity of identical limb elements can be joined in this way to form the cylindrical stent structure, as seen in FIG. 1.

Figure 5:
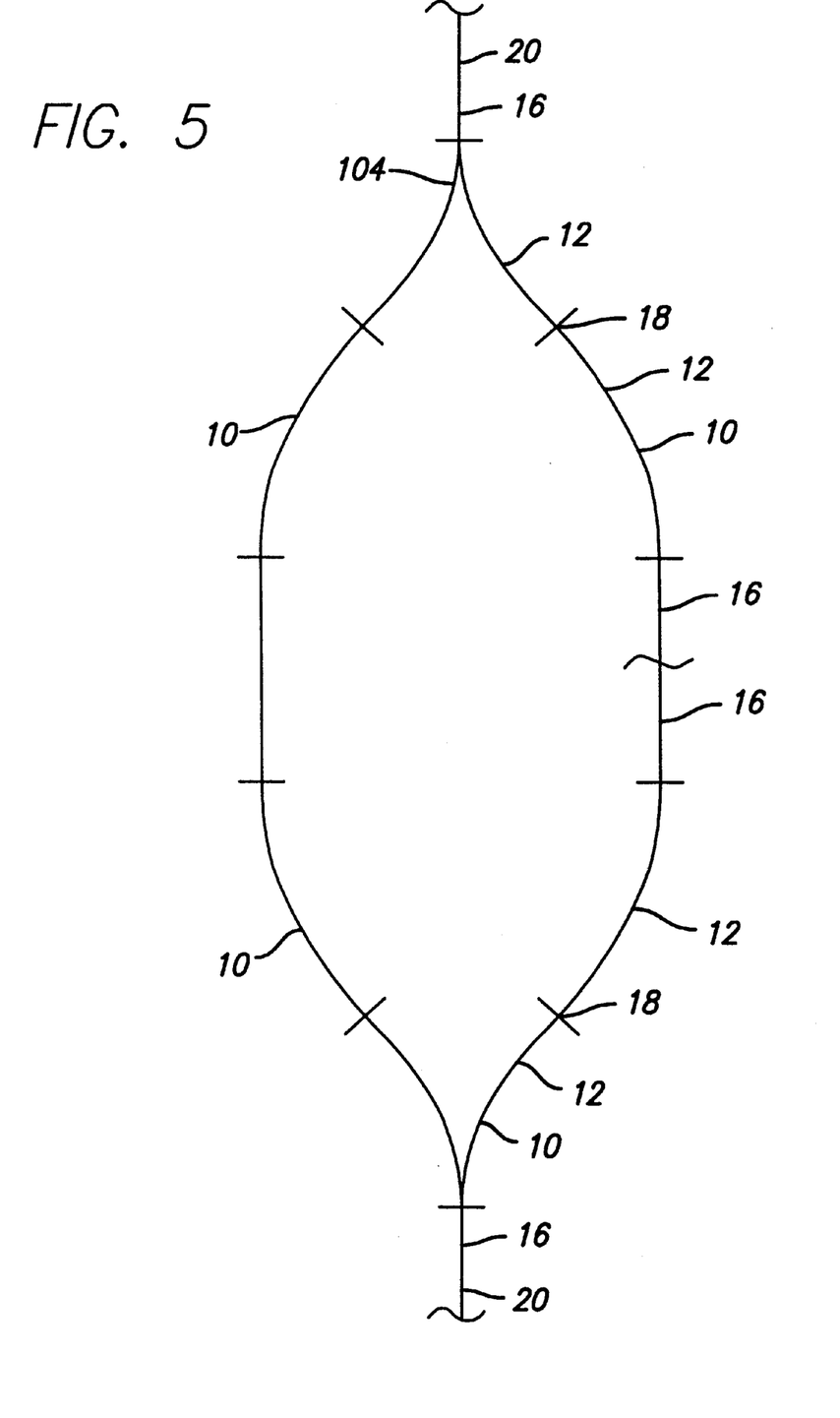
FIG. 5 is a side view, depicting an almond shaped stent cell of a stent to be used in the present invention.

Referring to FIG. 5, a stent cell 104 may have an almond-like shape and each cell 104 may embody four limb elements 10. Each limb 10 essentially comprises a quarter of a full stent cell 104. As described above, one limb 10, making up a quarter of the stent cell 104, starts from the midpoint of the stent cell 104 to the end of the stent cell 104. The limb elements 10 is comprised of two curve elements 12. These curve elements 12 are of equal radius, equal length and opposite direction. In a preferred stent embodiment, the limb 10 would be composed of two curves having constant radius r with an inflection point 18 in the middle where they reverse direction.

Under ideal conditions, it is preferred that the stress along the length of the limb 10 be as evenly distributed as possible so that there is minimal or no stress at the inflection point 18. Along the rest of limb 10, the stress level will be determined by the inverse of the radius r that the stent 8 limb has in its relaxed configuration. During introduction into vasculature, the stent 8 is compressed down into a catheter (not shown). In this compressed configuration, the curved limb elements 12 become generally straight. The change in radius r of curvature from the compressed state where the limbs 10 are straight to its profile in a relaxed state has a bearing on the amount of stress. The stress along the limb 10 and the amount of energy that can be stored in the stent 8 is determined by the change in the radius of curvature at any point along the limb 10.

Under previous stent heating processes, a stent is expanded over a cylindrical mandrel and heated. This process results in a smaller radius of curvature r value, for example, near the ends 16 of the limbs 10 and a much larger radius of curvature r value near the inflection point 18, which, in turn, results in higher stress near the straight segment elements 16 of the limb 10 than near the inflection point 18 of the limb 10. Therefore, optimum use of the material embodying the stent is achieved only near the straight segment elements 16 of the limb 10 and is not achieved near the inflection point 18.

What is to be achieved with the present mandrel invention is to increase the radius of curvature r at or near the point 20 where the limbs 10 meet as well as to decrease the radius r value near the inflection point 18. Ideally, it would be beneficial for the limb 10 to have one radius of curvature r value along the first curve 12 and the same but opposite radius of curvature r value in the second curve 12.

The mandrel of the present invention, cures the problems which have been experienced using prior art mandrels by having constraint mechanisms compress and hold one limb 10 next to an adjacent limb 10 near the straight segments 16. The result being an increase in the radius of curvature r at or near the joints 20 where the limbs meet and a decrease in the radius of curvature r value near the inflection point 18.

Figure 6:
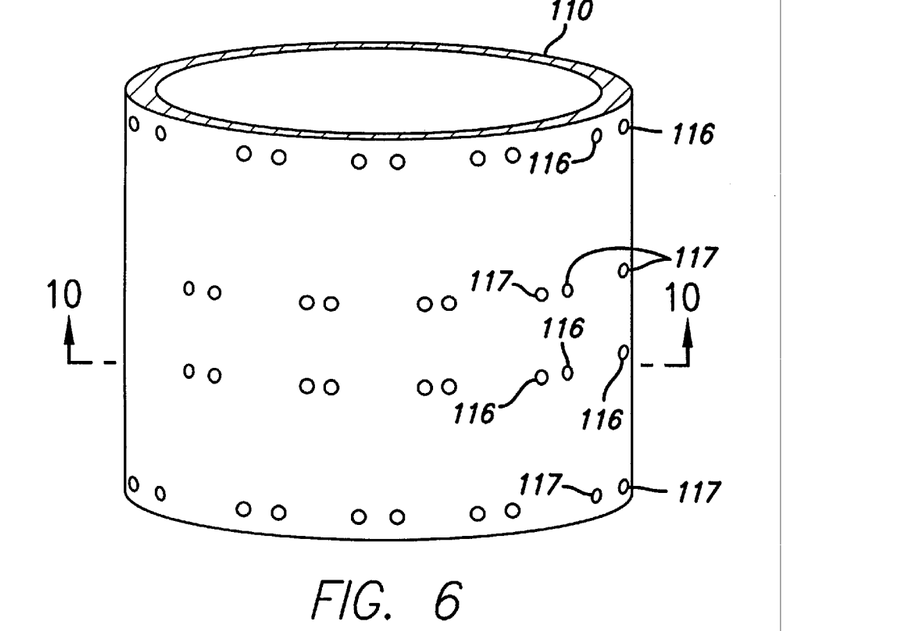
FIG. 6 is a perspective view, depicting a mandrel of the present invention having restraint pinholes radially drilled into an outer surface.

In a preferred embodiment, as shown in FIG. 6, the mandrel 110 is formed from a heat conducting metal, such as aluminum. The mandrel 110 is a thin-walled hollow cylinder with a multiplicity of pinholes 116 and 117 drilled into the mandrel 110 at various locations depending on the profile or design of the stent to be formed. Furthermore, the outer diameter of the mandrel 110 will depend on the inner diameter required by the stent designer. For illustration purposes, the mandrel 110 is shown including bottom straight segment restraint pinholes 117 and top straight segment restraint pinholes 116.

Figure 6A:
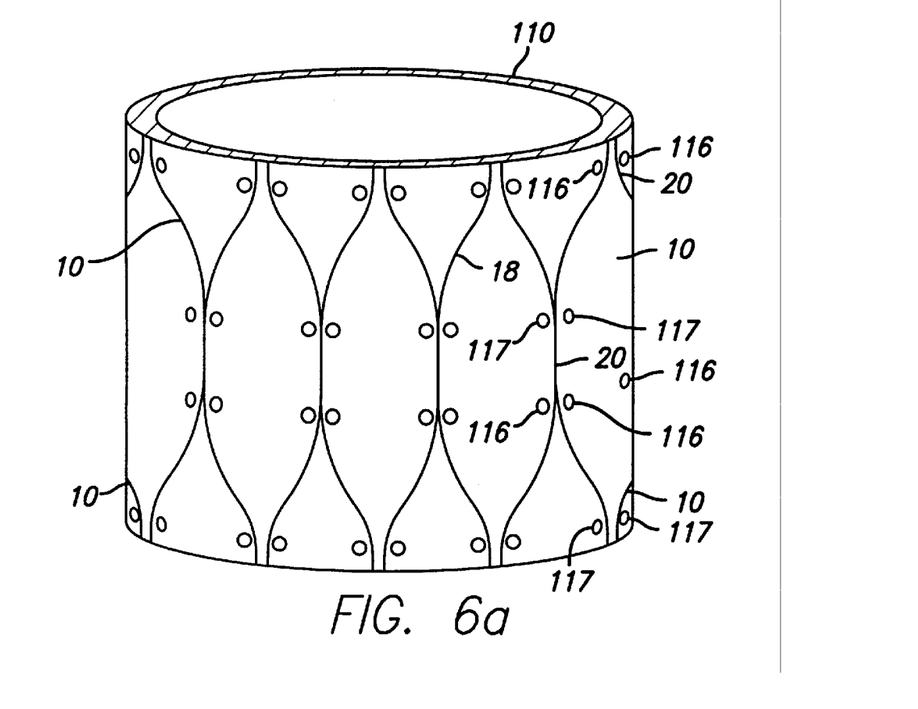
FIG. 6a is a perspective view, depicting the mandrel of FIG. 6 with a stent having curved limb elements mounted thereon.
Figure 10:
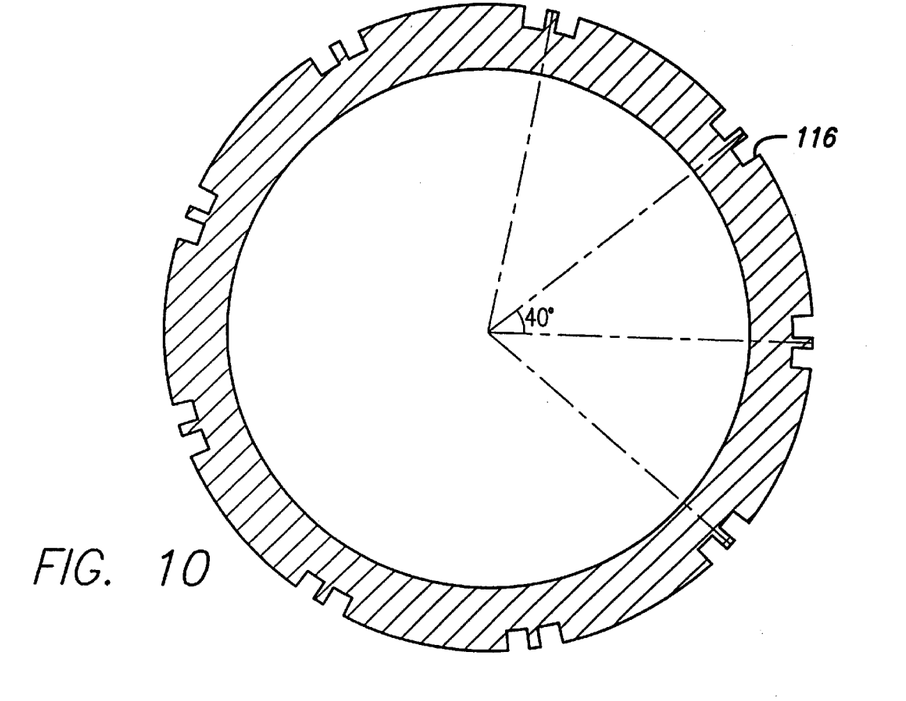
FIG. 10 is a cross sectional view taken along line 10—10 of FIG. 6, depicting the mandrel with drilled pinholes.

A cross-sectional view taken along line 10—10 of the mandrel 110 is shown in FIG. 10. Referring to FIG. 6a, a stent 8 is mounted on the mandrel 110 so that limb elements 10 are routed as desired between pinholes 116, 117. Pins 120 (see FIG. 8) are then placed within the pinholes 116, 117 to restrain the position of the limb elements 10. Alternatively, the stent 8 can be placed upon the mandrel 110 with the pins 120 already in place. Additionally, a separate mechanism (not shown) can be incorporated into the mandrel to cause The pin to automatically retract and project.

Figure 7:
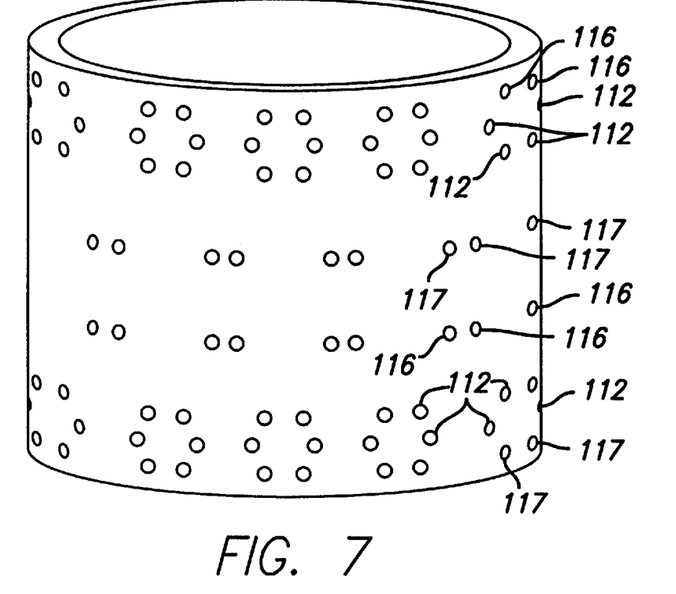
FIG. 7 is a perspective view, depicting an alternative embodiment of a mandrel of the present invention.
Figure 7A:
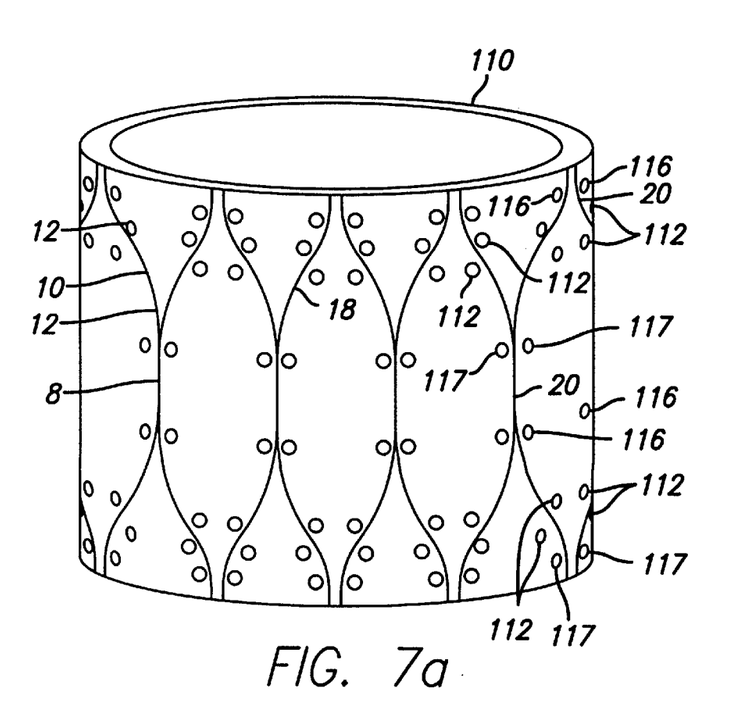
FIG. 7a is a perspective view, depicting the mandrel of FIG. 7 with a stent having curved limb elements mounted thereon.

Turning now to FIG. 7, there is shown optional restraint pinholes 112 which in conjunction with pins 120 (not shown) serve to further restrain the curved limb segments 12. These optional restraint pinholes 112 improve the final stent design by further facilitating restraining the stent 8 to the desired design. As can be seen from FIG. 7a, the optional restraint pinholes 112 are in close conformity with the curved segments 12 of the curved limb elements 10 and provide for closer constraint of the curved segments 12.

Figure 8:
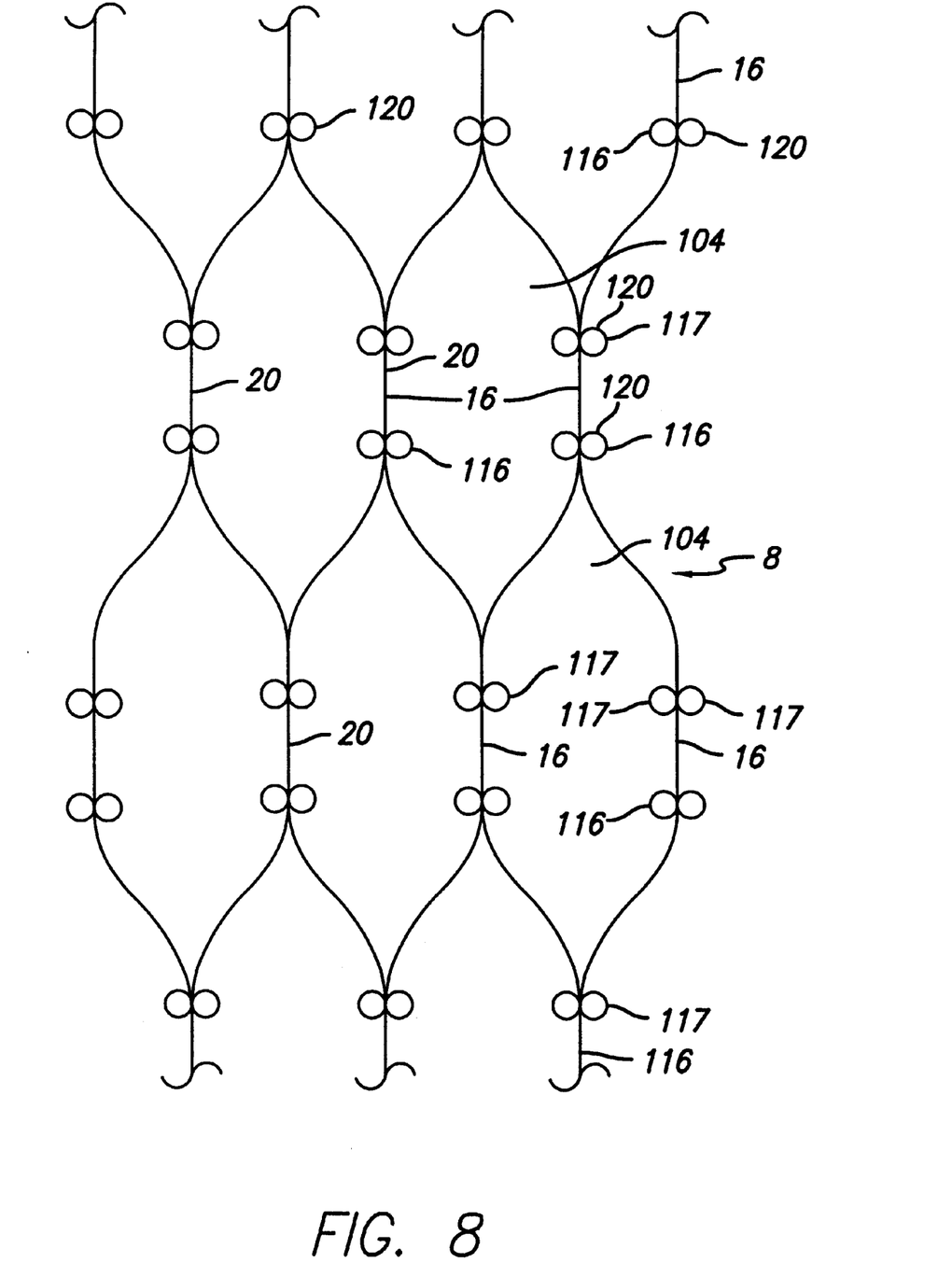
FIG. 8 is a side view, depicting a close up view of a stent routed between restraint pins.

Referring to FIG. 8, there is depicted a close up view of a stent 8 routed between pins 120 placed in bottom and top straight segment restraint pinholes 116 and 117. The pins 120 operate to restrain the short straight segments 16 of the stent limbs 10 and provide for receiving the straight segment limbs 16 of adjacent stent cells 104. As described above, the straight segment limbs 16 of adjacent stents cells 104 may be formed by cutting them from a tube or may alternatively be joined, either by welding, soldering, riveting, or gluing to form joint 20 when the stent 8 is formed from separate elements.

Figure 9:
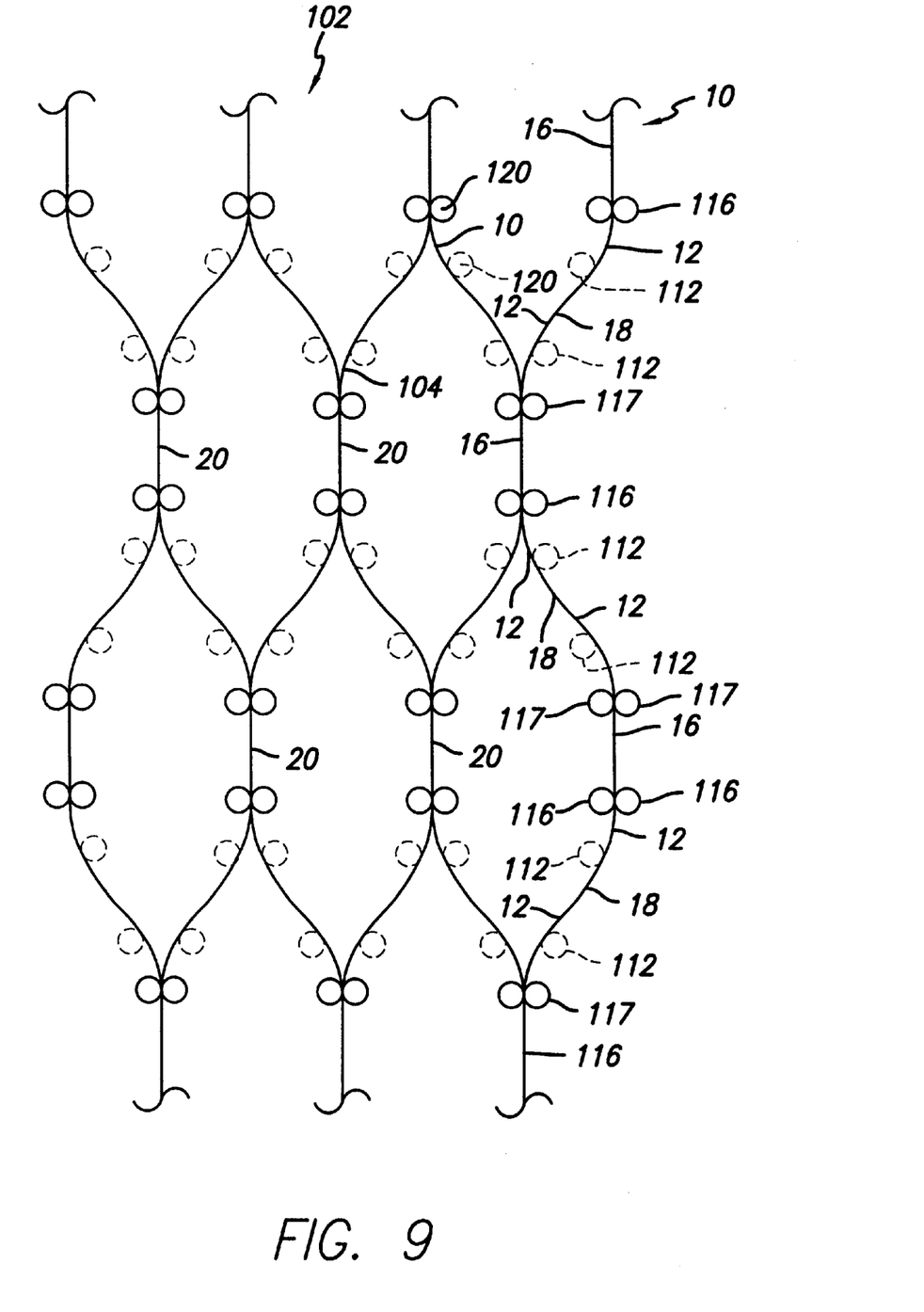
FIG. 9 is a side view, depicting a close up view of a stent routed between additional restraint pins.

It is contemplated that each of the pinholes 116 and 117 can be drilled 0.100" deep and 0.031" in diameter to receive restraint pins 120. FIG. 9 depicts the mandrel of FIG. 8 having in place optional restraint pinholes 112 corresponding to the curved limb elements 12 of the stent cell limb 10. These optional restraint pinholes 112 restrain and provide for proper curvature of the limb 10 curved segments 12. These optional restraint pinholes 112 are also drilled 0.100" deep and 0.031" in diameter to receive restraint pins 120.

Referring again to FIG. 8, there is shown a close up view of the stent 8 as it is positioned upon the mandrel with restraint pins 120 in place. As can be seen, the straight end segments 16 of the stent limb 10 are restrained and held together by pins 120 positioned in the straight segment restraint pinholes 116 and 117. Additionally, as shown in FIG. 9, the curve segments 12 of the stent limb 10 are restrained and held in position by pins 120 positioned in optional restraint pinholes 112.

The straight segment restraint pinhole pairs 116 and 117 are located slightly offset from the limb straight segments 16 of the stent cells 104 (See FIG. 8). Each of the straight segment restraint pinhole pairs 116 and 117 are spaced apart having a 0.024" gap. The curve segment optional restraint pinholes 112 are located in between the top and bottom straight segment restraint pinhole pairs 116 and 117 and correspond to the curve segments 12 of the stent limb 10 (See FIG. 9). All of the pins 120 have an outer diameter of 0.031".

The pins 120 which are positioned in the straight segment restraint pinhole pairs 116 retain the straight segments 16 of the stent limbs 10 at the stent endpoint 20. The pins 120 which are positioned in the curve segment optional restraint pinholes 112 provide for proper curvature of the curve segments 12 during the heating process. These pin sets form the restraint mechanism required for proper formation of a stent 8 having curved limbs and relieves the stress induced upon the stent 8 during the heating and setting of the stent frame shape.

In addition to the bottom straight segment restraint pinholes 116, top straight segment restraint pinholes 117 and curve segment optional pinholes 112, more pins may be utilized in additional pinholes which may be drilled into the outer surface of the mandrel 110 at points along the design of the stent cells 10. More pins would allow a more "exact" shape to be held.

Figure 11:
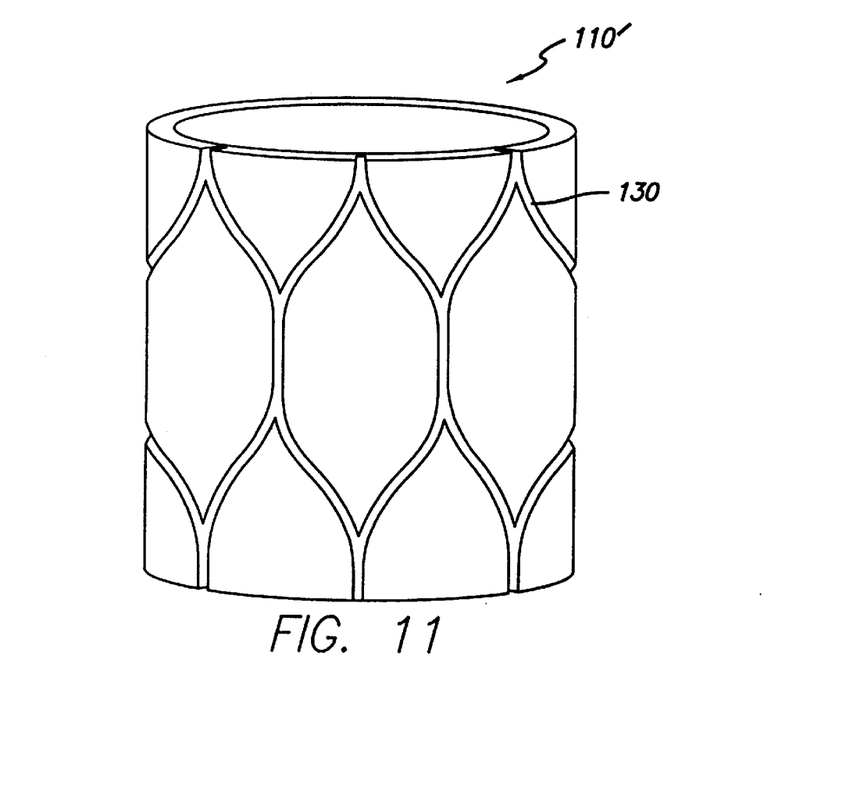
FIG. 11 is a perspective view, depicting another alternative embodiment of a mandrel of the present invention.

In an alternative embodiment as shown in FIG. 11, the mandrel 110' is formed from a heat conducting metal, such as aluminum. The mandrel 110' is a thin-walled hollow cylinder having shallow grooves 130 in the outer surface of the mandrel. The shallow grooves 130 are in the shape of a stent having curved limb elements and serves to restrain a mounted stent during the heating and setting process.

In use, a stent is placed on a mandrel of the present invention. The limb elements defining a body of the stent are routed between restraint mechanisms formed or placed on the mandrel. The stent is then subjected to a heating and setting procedure to thereby create a stent having a desired profile and stress distribution along the limbs of the stent. Heating and setting procedures vary for particular stent designs and stent materials but are in general, conventionally known in the art.

While several particular forms of the invention have been illustrated and described, it will also be apparent that various modifications can be made without departing from the spirit and scope of the invention. Accordingly, it is not intended that the invention be limited, except as by the appended claims.

We claim:

1. An apparatus for heating and setting elements of a stent, comprising:
   a mandrel having an outer surface; and
   a restraint mechanism which restrains and shapes a stent having curved limb elements each of which include at least two portions having equal but opposite radius of curvatures separated by an inflection point and further including shallow grooves, in the shape of the stent, in the outer surface of the mandrel.

2. The apparatus of claim 1, wherein said mandrel is a cylindrically hollow body made from a heat conducting metal.

3. The apparatus of claim 2, said restraint mechanism further comprises:
   a plurality of holes in said cylindrical shaped hollow body; and
   a plurality of pins configured in said holes.

4. The apparatus of claim 3, wherein said plurality of holes include top straight segment restraint hole pairs and bottom straight segment restraint hole pairs.

5. The apparatus of claim 4, wherein said plurality of holes include a plurality of curve segment holes.

6. The apparatus of claim 5, wherein said holes of said top hole pair and said bottom hole pair are spaced apart to form a 0.021" gap.

7. The apparatus of claim 6, further including a plurality of additional holes for receiving pins which provide for a more exact stent shape.

8. A method for forming a stent using a mandrel with a restraint mechanism embodying grooves formed in the mandrel, comprising the steps of:
   placing the stent on the mandrel;
   routing the limb elements within the grooves of the restraining mechanism such that the limb elements include at least two curved portions of equal but oppositely directed radius of curvatures separated by an inflection point; and
   applying heat to set a desired shape.

* * * * *